United States Patent
Taniguchi et al.

(10) Patent No.: US 10,400,007 B2
(45) Date of Patent: Sep. 3, 2019

(54) METHOD FOR PURIFYING ANTIBODY PROTEIN

(71) Applicant: ASAHI KASEI MEDICAL CO., LTD., Tokyo (JP)

(72) Inventors: Hiroki Taniguchi, Tokyo (JP); Masako Goto, Tokyo (JP); Ichiro Koguma, Tokyo (JP); Yoshiro Yokoyama, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 682 days.

(21) Appl. No.: 14/785,069

(22) PCT Filed: Apr. 15, 2014

(86) PCT No.: PCT/JP2014/060677
§ 371 (c)(1),
(2) Date: Oct. 16, 2015

(87) PCT Pub. No.: WO2014/171437
PCT Pub. Date: Oct. 23, 2014

(65) Prior Publication Data
US 2016/0083419 A1    Mar. 24, 2016

(30) Foreign Application Priority Data

Apr. 16, 2013 (JP) ................................. 2013-086123
Oct. 24, 2013 (JP) ................................. 2013-221510
Feb. 21, 2014 (JP) ................................. 2014-032149

(51) Int. Cl.
*B01D 15/36*    (2006.01)
*B01D 15/38*    (2006.01)
(Continued)

(52) U.S. Cl.
CPC .............. *C07K 1/22* (2013.01); *B01D 15/361* (2013.01); *B01D 15/362* (2013.01); *B01D 15/38* (2013.01);
(Continued)

(58) Field of Classification Search
CPC ... C07K 1/22; C07K 1/18; C07K 16/00; B01J 39/05; B01J 39/17; B01J 39/20;
(Continued)

(56) References Cited

U.S. PATENT DOCUMENTS 6,706,187 B1    3/2004    Okano et al.
2004/0134846 A1    7/2004    Akiyama et al.
(Continued)

FOREIGN PATENT DOCUMENTS

EP    2 889 617    7/2015
JP    2007-69193    3/2007
(Continued)

OTHER PUBLICATIONS

Hoffman, A.S., "Bioconjugates of intelligent polymers and recognition proteins for use in diagnostics and affinity separations," Clinical Chemistry, 46:9, pp. 1478-1486 (2000).*
(Continued)

*Primary Examiner* — Benjamin L Lebron
(74) *Attorney, Agent, or Firm* — Greenblum & Bernstein, P.L.C.

(57) ABSTRACT

A method for purifying a biologically active substance from a solution mixture containing impurities and the biologically active substance, in which an ion exchange chromatography carrier comprising a matrix and a copolymer containing at least N-isopropylacrylamide as a monomer unit and immobilized to a surface of the matrix is used, and the solution
(Continued)

mixture is allowed to flow through a container storing the carrier at a uniform temperature, thereby recovering the biologically active substance.

37 Claims, 5 Drawing Sheets

(51) Int. Cl.

| | | |
|---|---|---|
| *B01J 20/26* | (2006.01) | |
| *B01J 39/05* | (2017.01) | |
| *B01J 39/17* | (2017.01) | |
| *B01J 39/20* | (2006.01) | |
| *B01J 38/26* | (2006.01) | |
| *B01J 49/06* | (2017.01) | |
| *C07K 1/18* | (2006.01) | |
| *C07K 1/22* | (2006.01) | |
| *C07K 16/00* | (2006.01) | |
| *G01N 30/30* | (2006.01) | |
| *G01N 30/54* | (2006.01) | |
| *G01N 30/96* | (2006.01) | |
| *G01N 30/88* | (2006.01) | |
| *B01J 39/26* | (2006.01) | |
| *B01D 15/32* | (2006.01) | |
| *B01D 15/42* | (2006.01) | |

(52) U.S. Cl.
CPC ..... *B01D 15/3804* (2013.01); *B01D 15/3809* (2013.01); *B01D 15/3876* (2013.01); *B01J 20/26* (2013.01); *B01J 20/264* (2013.01); *B01J 20/267* (2013.01); *B01J 39/05* (2017.01); *B01J 39/17* (2017.01); *B01J 39/20* (2013.01); *B01J 39/26* (2013.01); *B01J 49/06* (2017.01); *C07K 1/18* (2013.01); *C07K 16/00* (2013.01); *G01N 30/30* (2013.01); *G01N 30/54* (2013.01); *G01N 30/96* (2013.01); *B01D 15/32* (2013.01); *B01D 15/327* (2013.01); *B01D 15/424* (2013.01); *G01N 2030/8813* (2013.01)

(58) Field of Classification Search
CPC ... B01J 39/26; B01J 39/19; B01J 49/06; B01J 20/285; B01J 20/3276; B01J 20/3278; B01J 20/32; B01J 20/267; B01J 20/26; B01J 20/264; B01D 15/18; B01D 15/1871; B01D 15/361; B01D 15/362; B01D 15/3809; B01D 15/3876; B01D 15/36; B01D 15/38; B01D 15/32; B01D 15/327; B01D 15/3804; B01D 15/424; G01N 30/30; G01N 30/54; G01N 30/96; G01N 30/461; G01N 2030/8813; C08F 293/005; C08F 2438/01; C08F 20/56; C08F 220/56; C08F 220/06; C08F 2/44; C08F 26/06; C08F 226/00; C08F 222/385; A61K 39/39591; C08H 1/00; C08J 3/12; C08J 3/24; C08J 2333/26; C08L 51/003; C08L 51/02; C08L 5/00; C08L 1/08; C08L 29/02; C08L 2555/80
See application file for complete search history.

(56) References Cited

U.S. PATENT DOCUMENTS

| | | | |
|---|---|---|---|
| 2004/0203149 A1* | 10/2004 | Childs | B01D 67/0006 |
| | | | 435/404 |
| 2005/0234166 A1* | 10/2005 | Lau | C08F 2/32 |
| | | | 524/211 |
| 2010/0181254 A1* | 7/2010 | Graalfs | B01D 15/362 |
| | | | 210/656 |
| 2011/0313066 A1* | 12/2011 | Jaber | C07K 1/30 |
| | | | 521/31 |
| 2012/0029154 A1* | 2/2012 | Deetz | B01J 20/264 |
| | | | 525/327.3 |
| 2012/0052550 A1 | 3/2012 | Woonton et al. | |
| 2012/0122759 A1* | 5/2012 | Brown | C07K 1/18 |
| | | | 514/1.1 |
| 2013/0317129 A1 | 11/2013 | Koguma et al. | |

FOREIGN PATENT DOCUMENTS

| | | |
|---|---|---|
| JP | 2009-85933 | 4/2009 |
| JP | 2011-41475 | 3/2011 |
| JP | 2011-174944 | 9/2011 |
| JP | 2012-502924 | 2/2012 |
| WO | 99-61904 | 12/1999 |
| WO | 01-74482 | 10/2001 |
| WO | 2012/081727 | 6/2012 |
| WO | 2012/121409 | 9/2012 |
| WO | 2013/187512 | 12/2013 |
| WO | 2014/034644 | 3/2014 |
| WO | 2014/065276 | 5/2014 |

OTHER PUBLICATIONS

Kanazawa, H., et al. "Temperature-responsive liquid chromatography. 2. effects of hydrophobic groups in N-isopropylacrylamide copolymer-modified silica", Analytical Chemistry, 69, pp. 823-830. (1997).*
Yoshida, R., et al. "Modulating the phase transition temperature and thermosensitivity in N-isopropylacrylamide copolymer gels", J. Biomater. Sci. Polymer. Edn, vol. 6, No. 6, pp. 585-598 (1994).*
Supplementary European Search Report issued with respect to Application No. 14785266.9, dated Jul. 19, 2016.
Nagase et al., "Preparation of Thermoresponsive Anionic Copolymer Brush for Thermally Modulated Adsorption/Elution of Proteins", *Polymer Preprints, Japan* vol. 58, No. 2, pp. 5116-5117 (3T1-13), 2009.
International Search Report issued in PCT/JP2014/060677, dated Jul. 15, 2014, along with an English language translation.
International Preliminary Report on Patentability issued in PCT/JP2014/060677, dated Oct. 20, 2015, along with an English language translation.

* cited by examiner

Fig. 5

| | Aggregate component(1) | | Aggregate component(2) | | Monomeric component(3) | | Aggregate adsorption rate (mg/mg) | Monomer recovery rate (mg/mg) | Total amount of antibody | | Flow rate (mL/min) | Carrier volume (mL) | Flow rate/carrier volume (mL/min·mL) |
| | Content (mg) | Content rate (%) | Content (mg) | Content rate (%) | Content (mg) | Content rate (%) | | | Antibody content (mg) | Antibody recovery rate (%) | | | |
|---|---|---|---|---|---|---|---|---|---|---|---|---|---|
| Solution mixture 1 | 0.67 | 1.2 | 0.95 | 1.7 | 54.44 | 97.1 | | | 56.06 | | | | |
| Example 1 Recovery solution (Protein A elution fraction) | 0.20 | 0.4 | 0.27 | 0.5 | 51.58 | 99.1 | 0.71 | 0.95 | 52.05 | 92.9% | 0.40 | 2.00 | 0.20 |
| Example 2 Recovery solution (Protein A elution fraction) | 0.17 | 0.4 | 0.09 | 0.2 | 44.90 | 99.4 | 0.84 | 0.82 | 45.16 | 80.6% | 0.40 | 2.00 | 0.20 |
| Solution mixture 2 | 1.30 | 0.5 | 3.12 | 1.2 | 255.95 | 98.3 | | | 260.38 | | | | |
| Example 3 Recovery solution (Protein A elution fraction) | 0.19 | 0.1 | 0.99 | 0.4 | 240.87 | 99.5 | 0.73 | 0.94 | 242.15 | 93.0% | 0.40 | 2.00 | 0.20 |
| Solution mixture 3 | 1.41 | 1.9 | 1.11 | 1.5 | 71.65 | 96.6 | | | 74.17 | | | | |
| Example 4 Recovery solution (Protein A elution fraction) | 0.18 | 0.3 | 0.24 | 0.4 | 60.71 | 99.3 | 0.83 | 0.85 | 61.14 | 82.4% | 6 | 0.6 | 10 |
| Solution mixture 4 | 0.44 | 1.5 | 0.26 | 0.9 | 28.8 | 97.6 | | | 28.79 | | | | |
| Example 5 (Protein A elution fraction) | 0.11 | 0.4 | 0.08 | 0.3 | 25.57 | 99.3 | 0.71 | 0.91 | 25.76 | 89.5% | 6 | 0.6 | 10 |
| Solution mixture 5 | 1.4 | 2.1 | 0.72 | 1.1 | 64.2 | 96.8 | | | 66.3 | | | | |
| Example 6 (Protein A elution fraction) | 0.05 | 0.1 | 0.19 | 0.3 | 56.63 | 99.6 | 0.89 | 0.88 | 56.9 | 85.8% | 6 | 0.6 | 10 |
| Solution mixture 6 | 1.86 | 2.0 | 1.61 | 1.7 | 90.41 | 96.3 | | | 93.88 | | | | |
| Example 7 (Protein A elution fraction) | 0 | 0.0 | 0.3 | 0.4 | 82.84 | 99.6 | 0.91 | 0.92 | 83.14 | 88.6% | 6 | 0.6 | 10 |
| Solution mixture 7 | 4.05 | 4 | 2.85 | 2.8 | 94.51 | 93.2 | | | 101.4 | | | | |
| Example 8 (Protein A elution fraction) | 0.11 | 0.13 | 0.48 | 0.54 | 85.1 | 99.3 | 0.91 | 0.9 | 85.69 | 84.5% | 1.5 | 0.25 | 6 |
| Solution mixture 8 | 2.29 | 2.3 | 2.36 | 2.4 | 95.62 | 95.4 | | | 100.26 | | | | |
| Example 9 (Protein A elution fraction) | 0 | 0 | 0.39 | 0.49 | 80.5 | 99.5 | 0.92 | 0.84 | 80.89 | 80.7% | 1.5 | 0.25 | 6 |
| Solution mixture 9 | 1.58 | 1.6 | 2.17 | 2.3 | 92.55 | 96.1 | | | 96.32 | | | | |
| Example 10 (Protein A elution fraction) | 0 | 0 | 0.35 | 0.45 | 78.51 | 99.6 | 0.91 | 0.85 | 78.87 | 80.2% | 1.5 | 0.25 | 6 |
| Solution mixture 10 | 2.34 | 1.8 | 3.57 | 2.8 | 123.43 | 95.4 | | | 129.38 | | | | |
| Example 11 (Protein A elution fraction) | 0.6 | 0.58 | 1.16 | 1.12 | 101.74 | 98.3 | 0.7 | 0.82 | 103.5 | 80.0% | 0.3 | 0.25 | 1.2 |
| Solution mixture 11 | 1.85 | 1.5 | 2.95 | 2.3 | 121.36 | 96.2 | | | 126.14 | | | | |
| Example 12 (Protein A elution fraction) | 0.51 | 0.51 | 1.13 | 1.14 | 97.63 | 98.3 | 0.66 | 0.8 | 99.27 | 79.0% | 0.3 | 0.25 | 1.2 |

METHOD FOR PURIFYING ANTIBODY PROTEIN

BACKGROUND OF THE INVENTION

Field of the Invention

The present invention relates to a purification technique for a biomolecule, more particularly to a method for purifying an antibody protein.

Description of the Related Art

Immunoglobulin (antibody protein) is a biologically active substance governing an immunoreaction. Recently, availability of antibody proteins in e.g., pharmaceutical products, diagnostic agents or separation and purification materials for the corresponding antigen proteins has increased. Antibody proteins can be obtained from blood of an immunized animal, a culture solution of cells having an antibody producibility or a culture solution of animal ascites. However, blood and a culture solution containing an antibody protein contain proteins other than the antibody protein or impurities (contaminants) derived from a culture solution for use in culturing cells. For this reason, a complicated and time-consuming operation is generally required for separating and purifying the antibody protein from impurities.

Liquid chromatography is an important tool for separating and purifying an antibody protein. As a chromatographic method for separating an antibody protein, e.g., gel filtration chromatography, affinity chromatography, ion exchange chromatography and reversed phase chromatography are known. An antibody protein is separated and purified by using these chromatographic methods in combination.

Ion exchange chromatography is a separation method by reversibly adsorbing counter ions present in a mobile phase by an ion exchange group immobilized on the surface of a matrix serving as a stationary phase. As the matrix, beads or membranes such as a flat membrane and a hollow fiber are employed. Solid adsorbents (stationary phase) produced by binding a cation exchange group or an anion exchange group to these matrixes are commercially available. Generally, a solid adsorbent having a cation exchange group has a property of mainly adsorbing an antibody protein and not adsorbing most of the contaminants and is thus used for concentrating and separating the antibody protein.

Cation exchange groups are roughly classified into weak cation exchange group such as a carboxyl group and a strong cation exchange group such as a sulfonate group. The adsorbent having a weak cation exchange group has a disadvantage in that if pH of the mobile phase is changed, the surface charge of the adsorbent changes and the binding capacity of antibody protein changes. Accordingly, if the adsorbent having the weak cation exchange group is used for separation/purification of the antibody protein, reproducibility of separation is poor and the recovery rate of the antibody protein may possibly decrease. In contrast, in the adsorbent having the strong cation exchange group, since the surface charge of the absorbent does not change even if the pH of the mobile phase changes, the binding capacity of antibody protein rarely changes. In industrial separation and purification process for the antibody protein, reproducibility of separation is severely required although it is difficult to maintain the pH of the mobile phase to be constant. For this reason, the adsorbent having the strong cation exchange group is used.

In a method for purifying an antibody protein using a conventional adsorbent having an ion exchange group, the antibody protein adsorbed to a stationary phase is generally allowed to elute by increasing the salt concentration of a mobile phase to weaken the electrostatic interaction between the antibody protein and the adsorbent. Herein, as the salt concentration of the mobile phase increases, the antibody protein tends to easily elute. However, if the salt concentration of the mobile phase increases, the hydrophobic interaction between protein molecules increases, with the result that associates and aggregates of the protein molecules tend to be easily formed. Likewise, there is a tradeoff between easiness in elution of the antibody protein and easiness in aggregation of the antibody protein. Because of this, it is difficult to specify the salt concentration of the mobile phase satisfying various conditions required for purification, such as recovery rate, concentration and elution rate of an antibody protein.

Then, in order to overcome problems of the conventional adsorbent having the ion exchange group, a temperature responsive adsorbent is proposed, which can release a biologically active substance such as an antibody protein adsorbed to a stationary phase, not by increasing the salt concentration of a mobile phase but by changing the effective density of an ion exchange group on the surface thereof by varying temperature.

Patent Literature 1 discloses a packing material containing a charged copolymer whose effective charge density on a stationary phase surface can be changed by varying temperature, a production method thereof and a temperature responsive chromatographic method using the packing material. Patent Literature 2 discloses a stationary phase of temperature responsive chromatography prepared by densely immobilizing a polymer, which changes hydration force within the temperature range of 0 to 80° C., to a surface of a matrix by an atom transfer radical polymerization method. Patent Literature 3 discloses a method for producing a temperature responsive chromatography carrier, which is characterized in that a charged polymer, which changes hydration force within the temperature range of 0 to 80° C., undergoes propagation reaction by an atom transfer radical method by using isopropyl alcohol as a solvent. Patent Literature 4 discloses a method for producing a liquid chromatography carrier having a charged polymer, which changes hydration force within the temperature range of 0 to 80° C., immobilized to a surface of a solid substance and capable of separating a biologically active high-molecular weight substance useful in biology, medicine and pharmaceutical fields in a particular condition including a water mobile phase. In Non Patent Literature 1, it is disclosed that a temperature responsive chromatography carrier having a carboxyl group and prepared by an atom transfer radical polymerization method and a production method thereof. This document discloses monomer compositions for use in the atom transfer radical polymerization method as a monomer composition optimized for lysozyme separation.

CITATION LIST

Patent Literature

Patent Literature 1: International Publication No. WO 99/061904
Patent Literature 2: Japanese Patent Laid-Open No. 2007-69193
Patent Literature 3: Japanese Patent Laid-Open No. 2009-85933

Patent Literature 4: International Publication No. WO 01/074482

Non Patent Literature

Non Patent Literature 1: Polymer Preprints, Japan Vol. 58, No. 2, 3T1-13 (2009)

However, the above documents do not clearly disclose a method of efficiently purifying a biologically active substance. The methods disclosed in the documents are not suitably applied to, for example, an industrial scale process for separating and purifying the biologically active substance. Then, an object of the present invention is to provide a method for efficiently purifying the biologically active substance.

SUMMARY OF THE INVENTION

The present inventors made research and development activities from various angles with a view toward solving the above problems. As a result, the present inventors found that a desired biologically active substance can be highly purified by bringing a solution mixture, which contains impurities and a biologically active substance, into contact with an ion exchange chromatography carrier which has a matrix and a copolymer containing at least N-isopropylacrylamide as a monomer unit and immobilized to a surface of the matrix or a temperature responsive ion exchange chromatography carrier at a particular temperature to allow the chromatography carrier to selectively adsorb the impurities.

According to an aspect of the present invention based on the finding of the present inventors, there is provided a method for purifying a biologically active substance from a solution mixture containing impurities and the biologically active substance, wherein an ion exchange chromatography carrier having a matrix and a copolymer containing at least N-isopropylacrylamide as a monomer unit and immobilized to a surface of the matrix is used, and the solution mixture is allowed to flow through a container storing the carrier at a uniform temperature, thereby recovering the biologically active substance.

According to another aspect of the present invention, there is provided a method for purifying a biologically active substance from a solution mixture containing impurities and the biologically active substance, wherein at least one temperature responsive ion exchange chromatography carrier is used, and the solution mixture is allowed to flow through a container storing the carrier at a uniform temperature, thereby recovering the biologically active substance.

According to another aspect of the present invention, there is provided a method for removing impurities from a solution mixture containing the impurities and a biologically active substance, wherein an ion exchange chromatography carrier having a matrix and a copolymer containing at least N-isopropylacrylamide as a monomer unit and immobilized to a surface of the matrix is used, and the solution mixture is allowed to flow through a container storing the carrier at a uniform temperature, thereby removing the impurities.

According to another aspect of the present invention, there is provided a method for removing impurities from a solution mixture containing the impurities and a biologically active substance, wherein at least one temperature responsive ion exchange chromatography carrier is used, and the solution mixture is allowed to flow through a container storing the carrier at a uniform temperature, thereby removing the impurities.

The present invention is never expected from the related art and development of the invention into a novel antibody separation system never ever present in related art is expected.

According to the method for purifying the biologically active substance of the present invention, it is possible to efficiently purify the biologically active substance. Particularly, the present invention makes it possible to efficiently purify the biologically active substance and efficiently remove the impurities without exposing the biologically active substance to low pH conditions or high temperature conditions, which inactivate the biologically active substance.

BRIEF DESCRIPTION OF THE DRAWINGS

FIG. 5 is a table showing the results of Examples 1 to 12.

DETAILED DESCRIPTION OF THE PREFERRED EMBODIMENT

Figure 1:
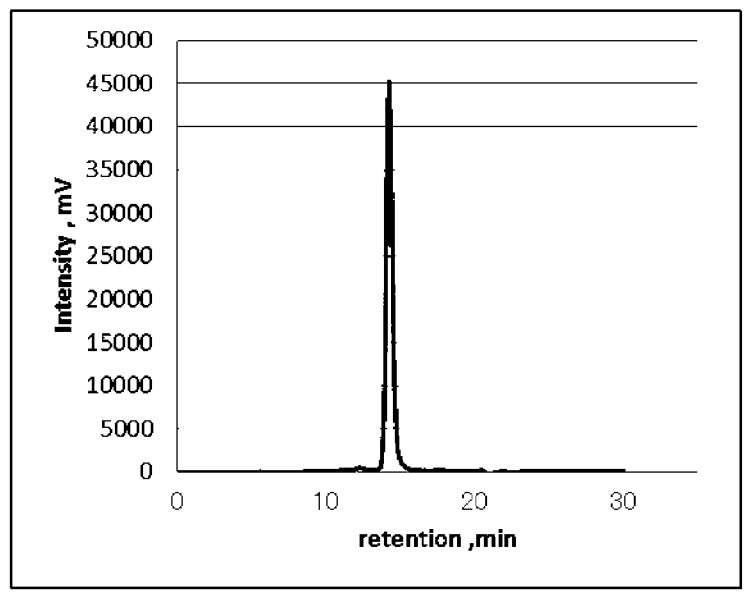
FIG. 1 is a graph showing absorbance obtained by subjecting an elution fraction from a protein A column according to Example 1 to size exclusion chromatography.

Preferred embodiments of the present invention (hereinafter referred to as "the embodiment") will be more specifically described below. Note that, in the following embodiment, an apparatus and method for embodying a technical idea of the invention will be described as examples; however, combinations of structural members are not specified as the following combination of members by the technical idea of the invention. The technical idea may be modified in various ways in the claims.

A method for purifying a biologically active substance according to the embodiment is a method for purifying a biologically active substance from a solution mixture containing impurities and the biologically active substance, wherein an ion exchange chromatography carrier having a matrix and a copolymer containing at least N-isopropylacrylamide as a monomer unit and immobilized to a surface of the matrix is used, and the solution mixture is allowed to flow through a container storing the carrier at a particular temperature, thereby recovering the biologically active substance. The particular temperature mentioned above preferably refers to a temperature, for example, at which impurities can be adsorbed in a mass fraction of 50% or more to a carrier and a biologically active substance can be recovered in a mass fraction of 70% or more.

The ion exchange chromatography carrier is hereinafter expressed as a solid adsorbent of ion exchange chromatography or a stationary phase of ion exchange chromatography. As the ion exchange chromatography carrier, for example, a temperature responsive cationic ion exchange carrier whose effective charge density on the surface of a stationary phase can be changed by varying temperature, is used.

The biologically active substance refers to, for example, a monomeric component of an antibody protein. The impurities refer to, for example, aggregate components of a dimer or a multimer of the antibody protein.

The temperature at which impurities can be adsorbed in a mass fraction of 50% or more to the carrier refers to a temperature at which the mass proportion of the impurities adsorbed to the carrier relative to the total amount of impurities contained in the solution mixture before supplied to the container storing the ion exchange chromatography carrier is 50% or more. Herein, as the temperature increases, the amount of impurities such as the aggregate components of the dimer or the multimer of the antibody protein to be adsorbed to the ion exchange chromatography carrier tends to increase. The mass proportion of impurities relative to the mass of the solution recovered is, for example, 2% or less and preferably 1% or less.

Furthermore, the temperature at which the biologically active substance can be recovered in the mass fraction of 70% or more refers to a temperature at which the mass proportion (hereinafter referred to also as "recovery rate") of the biologically active substance contained in the solution after it passes through the container storing the ion exchange chromatography carrier relative to the total amount of biologically active substance contained in the solution mixture before supplied to the container storing the carrier is 70% or more. Herein, as the temperature increases, the recovery rate of the biologically active substance such as the antibody protein monomeric component tends to decrease.

As the set temperature, at which the solution mixture of the impurities and the biologically active substance is allowed to flow through the container storing the carrier, a temperature, at which adsorptivity of a desired biologically active substance to be purified to the carrier is low and adsorptivity of the impurities to the carrier is high, is selected. The temperature region, in which the monomeric antibody protein is unlikely to be adsorbed to the cationic ion exchange carrier and the impurities is likely to be adsorbed to the carrier, is, for example, 5° C. or more and 60° C. or less, preferably 10° C. or more and 50° C. or less, more preferably 15° C. or more and 40° C. or less, further more preferably 20° C. or more and 35° C. or less and particularly preferably 25° C.

Herein, if the recovery rate of the desired biologically active substance is more important, the temperature is decreased; however, if the purity is more important, the temperature is increased. In this way, a desired product can be recovered by controlling temperature without changing a buffer, etc.

Depending upon the properties of the desired biologically active substance, a degree of the adsorption of the desired biologically active substance to be purified differs from that of impurities. Even in such a case, the desired biologically active substance can be recovered by controlling temperature without changing a buffer, etc.

Note that, at a site where a biologically active substance is purified, it is desired to use a chromatography carrier that can be used at room temperature conditions from 20° C. or more to 35° C. or less. This is because it is known that if a biologically active substance is exposed to a high temperature condition, the substance is denatured and loses its activity. Since it is difficult to accurately and uniformly control temperature in industrial production, it is highly demanded to use a chromatography carrier that can be used at room temperature at a uniform temperature.

An antibody protein as an example of the biologically active substance is a glycoprotein (also referred to as gamma globulin or immunoglobulin) produced by B lymphocytes serving as an infection protective mechanism of vertebrate animals, as is generally defined in biochemistry. For example, the antibody protein purified by the method according to the embodiment is used as a medicinal product for a human and has substantially the same structure as the antibody protein in the human body to which the product is administered.

The antibody protein may be a human antibody protein or an antibody protein derived from a mammal such as a bovine and mouse except a human. Alternatively, the antibody protein may be a chimeric antibody protein with human IgG and a humanized antibody protein. The chimeric antibody protein with human IgG refers to an antibody protein having a variable region derived from an organism except a human, such as a mouse, and the other region, i.e., a constant region, which is replaced so as to have immunoglobulin derived from a human. The humanized antibody protein refers to an antibody protein having a variable region whose complementarity-determining region (CDR) is derived from an organism except a human and whose framework region (FR) is derived from a human. The immunogenicity of the humanized antibody protein is lower than that of a chimeric antibody protein.

The class (isotype) and subclass of the antibody protein to be purified by the method according to the embodiment is not particularly limited. For example, antibody proteins are classified into five classes, i.e., IgG, IgA, IgM, IgD and IgE, depending upon the difference in structure of a constant region. However, the antibody protein to be purified by the method according to the embodiment may belong to any one of the five classes. Furthermore, in the human antibody protein, IgG, there are four subclasses, IgG1 to IgG4 and there are two subclasses IgA1 and IgA2 in IgA. However, the antibody protein to be purified by the method according to the embodiment may belong to any one of the subclasses. Note that an antibody associated protein such as Fc fusion protein produced by binding a protein to an Fc region may be included in the antibody protein to be purified by the method according to the embodiment.

The antibody proteins can be also classified by the origins. However, the antibody protein to be purified by the method according to the embodiment may be any one of a natural human antibody protein; and a recombinant human antibody protein, a monoclonal antibody protein, and a polyclonal antibody protein, which are produced by gene recombinant techniques. Of these antibody proteins, human IgG is preferable as the antibody protein to be purified by the method according to the embodiment, in view of demand and importance as an antibody medicament, but not limited to this.

The ion exchange chromatography carrier having the matrix and the copolymer containing at least N-isopropylacrylamide as the monomer unit and immobilized to the surface of the matrix, to be used in the purification method according to the embodiment preferably contains a cationic ion exchange group. The cationic ion exchange carrier according to the embodiment is formed, for example, by polymerizing a monomer composition containing a monomer having a cationic ion exchange group and/or cationic ion exchange group introducing precursor monomer and a N-isopropylacrylamide monomer by a polymerization method such as a surface living radical polymerization method and a radiation graft polymerization method, so as to extend from the matrix surface.

The presence of N-isopropylacrylamide can be specified by pyrolytic gas chromatography/mass spectroscopy (GC/MS). When a N-isopropylacrylamide homopolymer is analyzed by pyrolytic GC/MS, an isopropyl amine site and monomer sites of an isopropyl isocyanate and a N-isopropylacrylamide can be determined. When analysis results of an N-isopropylacrylamide homopolymer are compared to the analysis results of the ion exchange chromatography carrier to be used, whether or not N-isopropylacrylamide is contained as the monomer unit can be determined. When the peaks derived from other monomers are overlapped with the peak derived from N-isopropylacrylamide, analysis conditions may be modified e.g., by changing the length of the column or changing the column itself to overcome the overlap.

An ion exchange chromatography solid adsorbent having a temperature responsive cationic ion exchange carrier according to the embodiment contains, for example, a matrix and a temperature responsive copolymer immobilized to a surface of the matrix. The copolymer has at least a cationic ion exchange group. The temperature responsive cationic ion exchange carrier according to the embodiment is, for example, formed by polymerizing a monomer composition, which contains a monomer having a cationic ion exchange group and/or a cationic ion exchange group introducing precursor monomer and a monomer acquiring a temperature responsive property after polymerization, by a polymerization method such as a surface living radical polymerization method and a radiation graft polymerization method so as to extend from a surface of the matrix.

The monomer acquiring a temperature responsive property after polymerization, which refers to a monomer forming a polymer whose hydration force changes within the temperature range of 0 to 80° C. after polymerization, may include monomers forming a polymer having a lower critical solubility temperature (LCST) and a polymer having an upper critical solubility temperature (UCST) within the temperature range of 0 to 80° C. Homopolymers, copolymers of these or mixtures thereof may be used.

Examples of the shape of the matrix to be used in the embodiment, may include, but are not particularly limited to, beads shape and membrane shapes. Particularly, in the case where the matrix has the membrane shape, a pressure increase tends to be suppressed and the rate of a treatment tends to be improved. Furthermore, if the matrix has the membrane shape, since a whole treatment solution can be forced to pass through the micro pores of the carrier, a reduction in impurity removal performance depending upon the flow rate is low. Also in this respect, the rate of the treatment can be improved.

In the case where beads are employed as the matrix, beads having various particle sizes are available. The particle size of the bead matrix, which is not particularly limited, is, for example, 1 to 300 μm, preferably 10 to 200 μm and further preferably 20 to 150 μm. If the particle size is 1 μm or less, the beads are likely to be densely packed in a column (in which the carrier is charged), with the result that a solution tends not to be easily passed through the column at a high speed. In contrast, if the particle size is 300 μm or more, a space between the beads increases, leakage of a solution tends to occur when an antibody protein is adsorbed to the carrier.

Examples of the material for the bead matrix that can be used may include, but are not particularly limited to, glass, silica, a polystyrene resin, a methacrylic resin, crosslinked agarose, crosslinked dextran, crosslinked polyvinyl alcohol and crosslinked cellulose.

In the case where the matrix has the membrane shape, examples of the shape matrix may include a plate and a hollow fiber. In view of operability, the hollow fiber is preferable.

A material for a membrane matrix is not particularly limited; however, the material constituted of a polyolefin polymer is preferred in order to maintain mechanical properties. Examples of the polyolefin polymer may include homopolymers of an olefin such as ethylene, propylene, butylene and vinylidene fluoride, copolymers consisting of at least two types of olefins selected from these and copolymers consisting of at least one olefin and a perhalogenated olefin. Examples of the perhalogenated olefin may include tetrafluoroethylene and/or chlorotrifluoroethylene. Of them, polyethylene or polyvinylidene fluoride is preferable since it has excellent mechanical strength and can adsorb a large amount of contaminants such as proteins, and polyethylene is more preferable.

The matrix to be used in the embodiment, for example, has a plurality of micro pores. The diameter of the micro pores, which is not particularly limited, is for example, 5 to 1000 nm, preferably 10 to 700 nm and further preferably 20 to 500 nm. If the diameter of the micro pores is 5 nm or less, the molecular weight of antibody protein that can be separated tends to be low. In contrast, if the diameter of micro pores is 1000 nm or more, the surface area of the matrix decreases and the binding capacity of antibody protein tends to decrease.

In the embodiment, a polymer having a cation exchange group is immobilized to the matrix. Examples of the immobilization method may include, but are not limited to, an "atom transfer radical method," in which an atom transfer radical polymerization initiator is immobilized to a matrix surface and a temperature responsive polymer is allowed to grow (extend) from the initiator in the presence of a catalyst; and a "radiation graft polymerization method," in which radiation is applied to a matrix to generate radicals and a polymer is allowed to grow (extend) from the radicals generated as a starting point. As another immobilization method, there is a surface living radical polymerization method, i.e., an "atom transfer radical polymerization method," which is favorably used since a polymer is highly densely immobilized to a matrix surface.

When the polymer is immobilized to the matrix surface by the "atom transfer radical polymerization method," the initiator to be used herein is not particularly limited. When the matrix has a hydroxyl group, for example, 1-trichlorosilyl-2-(m,p-chloromethylphenyl) ethane, 2-(4-chlorosulfonyl-phenyl)ethyltrimethoxysilane, (3-(2-bromoisobutyryl)propyl)dimethylethoxysilane and 2-bromoisobutyryl bromide are used. A polymer chain is grown (extended) from the initiator. Examples of the catalyst to be used herein may include, but are not particularly limited to, copper halides (CuIX) such as CuICl and CuIBr. Examples of a ligand complex to the copper halide may include, but are not particularly limited to, tris(2-(dimethylamino)ethyl)amine ($Me_6$TREN), N,N,N'',N'''-pentamethyl diethylene triamine (PMDETA), 1,1,4,7,10,10-hexamethyltriethylenetetraamine (HMTETA), 1,4,8,11-tetramethyl 1,4,8,11-azacyclotetradecane ($Me_4$Cyclam) and bipyridine.

When the polymer is immobilized to the matrix surface by the "radiation graft polymerization method," any means may be used for generating radicals from the matrix. Application of ionizing radiation to the matrix is preferable since radicals are uniformly generated over the entire matrix. Examples of the ionizing radiation that can be used may include γ ray, electron ray, β ray and neutron ray. Electron ray or γ ray are preferable for industrial use. The ionizing radiation can be obtained from radioisotopes such as Cobalt-60, strontium 90 and cesium-137 or by means of e.g., an X-rays imager, an electron ray accelerator and an ultraviolet irradiation device.

The irradiation dose of ionizing radiation is preferably 1 kGy or more and 1000 kGy or less, more preferably 2 kGy or more and 500 kGy or less and further preferably 5 kGy or more and 200 kGy or less. If the irradiation dose is less than 1 kGy, radicals tend not to be uniformly generated. In contrast, if the irradiation dose exceeds 1000 kGy, the physical strength of the matrix tends to decrease.

Generally, graft polymerization methods by application of ionizing radiation are roughly divided into a pre-irradiation method, in which radicals are generated from a matrix and then the radicals are brought into contact with a reactive compound, and a simultaneous irradiation method, in which radicals are generated from a matrix in the state where a membrane is in contact with a reactive compound. In the embodiment, either one of the methods can be applied; however, the pre-irradiation method producing a smaller amount of oligomer is preferable.

In the embodiment, the solvent to be used for polymerization is not particularly limited as long as it can uniformly dissolve a reactive compound. Examples of the solvent may include an alcohol such as ethanol, isopropanol and t-butyl alcohol, an ether such as diethyl ether and tetrahydrofuran, a ketone such as acetone and 2-butanone, water or a mixture of these.

The polymer to be immobilized to the matrix surface, for example, has an N-isopropylacrylamide. A poly(N-isopropylacrylamide) is known to have a lower critical temperature of 32° C. A solid adsorbent prepared by introducing a polymer having an N-isopropylacrylamide into a matrix surface greatly varies in surface physical property, i.e., hydrophilic/hydrophobic property, at a critical temperature. Due to this, if a solid adsorbent is prepared by grafting or applying a polymer having a N-isopropylacrylamide to the surface of a chromatography packing material, the force of the solid adsorbent holding an antibody protein can be changed depending upon temperature. As a result, the holding behavior of the solid adsorbent can be controlled by temperature without changing the composition of the eluate.

To control the lower critical temperature to be 32° C. or more, a monomer, which is more hydrophilic than isopropyl acrylamide, such as acrylamide, methacrylic acid, acrylic acid, dimethyl acrylamide and vinyl pyrrolidone (serving as a hydrophilic comonomer) may be copolymerized with a N-isopropylacrylamide.

In contrast, to control the lower critical temperature to be 32° C. or less, a hydrophobic monomer such as styrene, alkyl methacrylate and alkyl acrylate (serving as a hydrophobic comonomer), may be copolymerized with a N-isopropylacrylamide.

When the matrix is the hollow fiber, if the temperature of the treatment in the flow-through operation is low, impurity removal performance tends to deteriorate and the amount of antibody treatment, which represents the amount of antibody that can be purified, tends to decrease. If the treatment is performed at a high temperature, the amount of antibody treatment increases; however, the antibody is likely to be aggregated at a high temperature. For this reason, when the temperature responsive polymer is polymerized, the hydrophobic monomer is desirably copolymerized to decrease the lower critical temperature. The proportion of hydrophobic monomer relative to the total monomer herein in order to decrease the treatment temperature, is for example, 2% or more, preferably 5% or more, more preferably 10% or more and further preferably 20% or more.

The polymer to be immobilized to the matrix surface has, for example, a strong cation exchange group such as a sulfonate group (as a cation exchange group). A method for providing the strong cation exchange group is not particularly limited. As a first method, a method of copolymerizing so as to contain a monomer having the strong cation exchange group in synthesizing a polymer chain to be immobilized to the matrix surface is mentioned. Examples of the monomer unit having the sulfonate group may include structural units of a polymer having the sulfonate group, such as (meth)acrylamide alkyl sulfonate, vinyl sulfonate, acrylamide t-butyl sulfonate and styrene sulfonate.

If at least part of a monomer unit of a copolymer is derived from a vinyl monomer having a sulfonate group such as vinyl sulfonate, the sulfonate group is bound to a main chain not through a linker. In this case, hydrophobic interaction between the linker and an antibody protein is not produced and thus the antibody protein tends not to be adsorbed to a matrix surface. Note that at least part of the monomer unit of the copolymer having the strong cation exchange group can be represented by the following formula (1)

  (1)

where $R_1$, $R_2$, $R_3$ are each individually represent H or Me.

In the embodiment, as a second method for providing the strong cation exchange group to the polymer to be immobilized to the matrix surface, a method in which copolymerization is made so as to contain a monomer having a "strong cation exchange group introducing precursor" and the precursor is converted into the sulfonate group, is mentioned. Note that "strong cation exchange group introducing precursor" may include a "strong cation exchange group precursor." The "strong cation exchange group precursor" is, for example, a strong cation exchange group provided with a protecting group. Examples of the monomer having the sulfonate group precursor may include, but are not limited to, phenyl vinyl sulfonate.

In the embodiment, as a third method for providing the strong cation exchange group to the polymer to be immobilized to the matrix surface, a method in which copolymerization is made so as to contain a monomer having a functional group capable of providing the strong cation exchange group as the strong cation exchange group introducing precursor monomer and then the functional group capable of providing the strong cation exchange group is converted into the sulfonate group, is mentioned. Examples of the monomer having the functional group capable of providing the strong cation exchange group may include styrene and glycidyl methacrylate. When a monomer having a strong cation exchange group is polymerized by the surface living radical polymerization method, a sufficient polymerization rate is not frequently obtained; however, a sufficient polymerization rate can be obtained by using the strong cation exchange group introducing precursor monomer at least partly containing a methacrylic acid derivative or an acrylic acid derivative, such as glycidyl methacrylate.

If at least part of the monomer unit of the copolymer having the strong cation exchange group is the methacrylic acid derivative or the acrylic acid derivative, hydrophobic interaction between the matrix or the other part of the copolymer and impurities such as aggregates is increased, with the result that the amount of impurities such as aggregates to be adsorbed can be enhanced.

If the at least part of the monomer unit of the copolymer having the strong cation exchange group is the methacrylic acid derivative or the acrylic acid derivative, the at least part of the monomer unit of the copolymer having the strong cation exchange group has a group represented by the following formula (2) or (3).

  (2)

  (3)

The sulfonate group of the monomer unit represented by the above formula (2) is bound to a main chain via a linker containing at least —CH(—OH)—CH$_2$—. The sulfonate group of the monomer unit represented by the above formula (3) is bound to a main chain via a linker containing at least —CH—. Since steric hindrance is mitigated by the presence of the linker, impurities such as aggregates may possibly quickly bind to the sulfonate group.

In the embodiment, a monomer composition having a proportion of a monomer having the strong cation exchange group and/or the strong cation exchange group introducing precursor monomer relative to N-isopropylacrylamide within the range of 0.01 to 500.00 mol % is polymerized in accordance with a surface graft polymerization method. By this, the copolymer contains the strong cation exchange group in a proportion of 0.01 to 500.00 mol % relative to N-isopropylacrylamide in terms of monomer. The above proportion is preferably 0.1 to 400.0 mol %, more preferably 1 to 300.0 mol %, further preferably 1.5 to 200.0 mol % and most preferably 4 to 150 mol %. If the above proportion exceeds 500.00 mol %, the amount of antibody protein to be adsorbed increases, with the result that the recovery rate of the antibody protein tends to decrease. On the other hand, if the above proportion is less than 0.01 mol %, the amount of introduced strong cation exchange group is extremely low, with the result that amount of impurities such as aggregates to be adsorbed to the solid adsorbent itself tends to decrease.

The mass proportion of N-isopropylacrylamide in the copolymer is desirably 1% to 99%, preferably 10% to 90%, more preferably 20% to 80% and further preferably 30 to 70%. If the proportion of N-isopropylacrylamide is small, temperature responsiveness extremely decreases, with the result that balance between the recovery rate and the purity of the recovered antibody tends not to be controlled by controlling temperature. In contrast, if the proportion of N-isopropylacrylamide is large, the temperature responsiveness is strong, in other words, copolymer is very sensitive to temperature, with the result that it becomes difficult to operate the resultant chromatography. If the proportion is 20% to 80% and further 30 to 70% or less, aggregates tend to be efficiently removed at room temperature without controlling temperature.

After the cation exchange carrier is used for the antibody purification, its resistance against regeneration with alkali tends to increase. For this reason, the sulfonate group density of the cation exchange carrier is desirably 30 mmol/L or more.

In the embodiment, the copolymerization proportion (composition) of the monomer unit having the strong cation exchange group relative to N-isopropylacrylamide can be obtained by analyzing the copolymer immobilized to the matrix surface. The copolymerization proportion can be analyzed by using various analytical methods such as an element analysis and NMR. After the copolymer is isolated from the matrix, the copolymerization proportion is analyzed. This is preferable in view of analytical precision because the effect of the matrix upon analysis can be eliminated. If the copolymer cannot be isolated from the matrix, the copolymer is polymerized in a solution without using the matrix to obtain the copolymer to be subjected to analysis of the copolymerization proportion.

The polymer immobilized to the matrix surface causes hydration and dehydration by changing temperature. The temperature range thereof is, for example, from 0° C. to 80° C. If the temperature exceeds 80° C., water is vaporized since a mobile phase consists of water, with the result that workability tends to deteriorate. In contrast, if the temperature is lower than 0° C., the mobile phase tends to be frozen.

The solid adsorbent obtained by the embodiment, is stored in a column of a common liquid chromatographic apparatus and used as a liquid chromatography system. A method for applying temperature to the solid adsorbent herein is not particularly limited. For example, the solid adsorbent may be brought into contact with an aluminum block, a water bath and an air layer controlled to be a uniform temperature or a solid adsorbent may be fit to a jacket, etc.

If the antibody protein is purified by use of the solid adsorbent according to the embodiment, a flow-through (FT) method is used, in which a monomeric component of a desired antibody protein is allowed to pass through the solid adsorbent within a temperature region and aggregate components are allowed to adsorb, with the result that the monomeric component of the antibody protein alone is substantially eluted. The amount of antibody protein to be provided to the solid adsorbent may be beyond or lower than the amount of impurities that can be adsorbed by the solid adsorbent. Since the aggregate of the antibody protein is largely charged than the monomer, binding of the aggregate to an ion exchange resin tends to be stronger than the binding to the monomer. In addition, since the hydrophobicity of the aggregate is stronger than that of the monomer, the aggregate interacts (hydrophobic interaction) with the hydrophobic portion of the solid adsorbent and binding to the solid adsorbent tends to be strong.

As the mobile phase of chromatography according to the embodiment, a neutral buffer may be used and an organic solvent is not required. The buffer herein is an aqueous solution containing inorganic salts, more specifically, examples may include a phosphate buffer, tris buffer and acetate buffer; however, the buffer is not particularly limited as long as it is usually used. The concentration of inorganic salts is satisfactorily 1 to 50 mmol/L, preferably 3 to 40 mmol/L and further preferably 5 to 30 mmol/L.

If the concentration of inorganic salts in a buffer is lower than 1 mmol/L, the activity of a solute, i.e., an antibody protein, tends to be damaged. Furthermore, if the concentration of inorganic salts in a buffer is lower than 1 mmol/L, the degree of dissociation of an ion exchange group on the surface of a temperature responsive adsorbent increases, and an antibody protein is tightly adsorbed to the surface of the temperature responsive adsorbent surface, with the result that the recovery rate of the antibody protein tends to decrease.

If the concentration of inorganic salts in a buffer is higher than 50 mmol/L, the degree of dissociation of an ion exchange group on an adsorbent surface decreases, with the result that it tends to be difficult to hold impurities such as aggregates on the adsorbent surface. As a result, it tends to be difficult to efficiently separate the antibody protein from the aggregate component. If the concentration of inorganic salts can be expressed in terms of electric conductivity, the electric conductivity of the inorganic salts is preferably 0.5 to 20 mS/cm, more preferably 0.5 mS/cm to 10 mS/cm and further preferably 0.5 mS/cm to 5 mS/cm.

The hydrogen ion concentration (pH) of the buffer is, for example, 3.0 to 9.0, preferably 4.5 to 8.5, further preferably, 5.0 to 8.0 and particularly preferably 5.0 to 7.5. If the pH of the buffer is higher than 9.0, electrostatic repulsion of antibody protein molecules tends to decrease and aggregation is easily caused. If the pH is lower than 3.0, an antibody protein is denatured, and reduction in activity and quality degradation such as generation of an aggregate tends to occur.

The flow rate of the solution mixture during the flow-through operation, is for example, a volume 0.1 times or more the volume of an ion exchange chromatography carrier/minute and a volume 30 times or less the volume of a carrier/minute, and preferably a volume the same as or more than the volume ion exchange chromatography carrier/minute and a volume 10 times or less the volume of a carrier/minute. In the case of hollow fiber matrix, since treatment efficiency is high, a high flow rate can be attained. However, when the flow rate exceeds a volume 30 times the volume of a carrier/minute, impurity removal property tends to decrease. In contrast, in the case of a bead matrix, the flow rate is particularly 0.1 times or more the volume of a carrier/minute and 3 times or less the volume/minute, 0.1 times or more the volume/minute and twice or less the volume/minute, and preferably 0.1 times or more the volume/minute and the same volume/minute or less. This is because if the flow rate exceeds 3 times the volume/minute, an antibody solution passes the space between beads without being in contact with the beads, with the result that impurity removal property tends to decrease.

At the temperature, at which the impurities can be adsorbed in a mass fraction of 50% or more to the cationic ion exchange carrier according to the embodiment mentioned above and the biologically active substance can be recovered in a mass fraction of 70% or more, the aggregates of the antibody protein are allowed to adsorb and the monomer of the antibody protein is recovered from the cationic ion exchange carrier. In this manner, the monomer of the antibody protein can be efficiently purified while suppressing generation of the aggregates of the antibody protein. Thus, according to the method for purifying the antibody protein of the embodiment, an extremely useful antibody protein to be used in medicinal products can be efficiently purified.

The present inventors further found that if the solution mixture containing the impurities and the biologically active substance is subjected to a purification process by affinity chromatography before the biologically active substance is purified by the ion exchange chromatography carrier, the amount of impurities can be reduced and purification can be more effectively performed by the ion chromatography carrier. The present inventors found that owing to this method, since the contact time of the antibody with the carrier can be reduced and the temperature of the antibody purified can be returned to an appropriate temperature immediately, the antibody can be efficiently purified while suppressing denaturation of the antibody. In the affinity chromatography, a protein A carrier, an acid elution type affinity chromatography carrier or a temperature responsive affinity chromatography carrier can be used.

In the embodiment, if the temperature responsive affinity chromatography carrier has temperature responsive protein A, which is modified protein A so as to change affinity for an antibody depending upon the temperature, temperature responsive protein A can be prepared with reference to Patent Document (WO2008/143199).

In the embodiment, a coupling reaction between NHS activated carboxyl group and temperature responsive protein A is, for example, performed as follows. First, a temperature responsive protein A solution (0.1 to 100 mg/mL) is prepared by using a buffer containing no amino group component such as a citrate buffer (pH 3.0 to 6.2), an acetate buffer (pH 3.6 to 5.6), a phosphate buffered saline (PBS, pH 5.8 to 8.5) or a carbonate buffer (pH 9.2 to 10.6). When the resultant aqueous solution is brought into contact with an active ester surface, a functional group such as an amino group contained in temperature responsive protein A reacts with the active ester to form an amide bond. As a result, temperature responsive protein A is immobilized to the surface via a covalent bond. The contact time herein may be set within the range of 2 minutes to 16 hours. After temperature responsive protein A is immobilized, it is desirable to wash the carrier with an appropriate washing solution. The washing solution used herein is desirably a buffer containing about 0.5 mol/L of salt (NaCl) and about 0.1% of a nonionic surfactant. This is because temperature responsive protein A physically adsorbed and not covalently bound can be removed.

After temperature responsive protein A is immobilized to the carrier surface (preferably, after temperature responsive protein A immobilized carrier is further washed), it is preferable that an unreacted carboxyl group or an active ester is allowed to bind to a low-molecular weight compound having an amino group to convert the carboxyl group or active ester into a functional group having a lower reactivity. In this manner, it is possible to prevent immobilization of undesirable molecules such as impurities that are substances not to be purified to the carrier surface. In a particular case where the terminal functional group of the temperature responsive protein A immobilizing carrier is an active ester, it is preferably to employ this operation.

In the specification, an operation for reacting the low-molecular weight compound having the amino group with the active ester group may be sometimes described particularly as "blocking." It should be noted that it is desirable that the carrier surface obtained after the carboxyl group or active ester is reacted with the low-molecular weight compound is hydrophilic. This is because the hydrophilic surface generally has an effect of suppressing nonspecific adsorption of a bio-related substance. For this purpose, it is preferable to use a low-molecular weight compound having an amino group further containing a hydrophilic group other than the amino group as the low-molecular weight compound containing the amino group. Examples of such the low-molecular weight compound may include, but are not limited to, ethanolamine, trishydroxymethylaminomethane and diglycolamine (IUPAC name: 2-(2-aminoethoxy)ethanol). Such a low-molecular weight compound is dissolved in a buffer such as PBS so as to obtain a concentration of 10 to 1,000 mmol/L and the solution is brought into contact with the carrier having temperature responsive protein A immobilized thereto. The reaction temperature may be set at 4 to 37° C. and the reaction time within the range of 2 minutes to 16 hours, for example.

The temperature responsive protein A immobilized carrier is stored in a preservative solution, i.e., a neutral solution, within the range of pH 4 to 8 at a low temperature of about 2 to 10° C. As the preservative solution, 20% ethanol is preferable in view of antibacterial activity.

Temperature responsive protein A has a property of binding to an antibody at a low temperature and releasing the antibody at a higher temperature than the temperature in binding. The temperature at which the property of temperature responsive protein A changes is previously confirmed, and adsorption and desorption of an antibody is preferably performed by changing temperature around the temperature. The temperature region in which an antibody is adsorbed to temperature responsive protein A is a low temperature region, for example, 0° C. or more and 20° C. or less, preferably 1° C. or more and 15° C. or less and most preferably 2° C. or more and 13° C. or less. The temperature region in which an antibody is desorbed from temperature responsive protein A is a high temperature region, for example, 20° C. or more and 60° C. or less, preferably 25° C. or more and 50° C. or less and most preferably 30° C. or more and 45° C. or less.

Example 1

The embodiment will be more specifically described based on Examples; however these Examples should not be construed as limiting the embodiment.

In Example 1, a cationic ion exchange carrier having a sulfonate group in the form of beads was synthesized by the atom transfer radical polymerization method.

1) Immobilization of Initiator

Crosslinked polyvinyl alcohol beads (1 g) (particle size: 100 μm) were moistened with pure water and placed in a 300 mL-conical flask made of glass. To the conical flask, 200 mL of tetrahydrofuran (containing no stabilizer, manufactured by Kanto Chemical Co., Inc.), 1.23 mL of 2-bromoisobutyryl bromide (manufactured by Tokyo Chemical Industry Co., Ltd.) and 1.40 mL of triethylamine (manufactured by Wako Pure Chemical Industries, Ltd.) were added. The mixture was shaken at room temperature for 16 hours. After completion of the reaction, the reaction mixture was filtered, washed three times with 200 mL of ethanol, and stored in dehydrated isopropanol. In this manner, an atom transfer radical polymerization (ATRP) initiator, i.e., 2-bromoisobutyryl bromide, was introduced into the surface of the crosslinked polyvinyl alcohol beads.

2) Surface Graft Polymerization

A monomer composition containing a precursor monomer of a sulfonate group, i.e., glycidyl methacrylate (GMA, manufactured by Tokyo Chemical Industry Co., Ltd.) in a proportion of 1 mol % relative to N-isopropylacrylamide was prepared. More specifically, 18.40 g of N-isopropylacrylamide (IPAAm, manufactured by Wako Pure Chemical Industries, Ltd.), 0.231 g of GMA, 1.217 g of butyl methacrylate (BMA, manufactured by Tokyo Chemical Industry Co., Ltd.), 0.085 g of copper(I) chloride (CuCl, manufactured by Wako Pure Chemical Industries, Ltd.) and 0.012 g of copper(II) chloride ($CuCl_2$, manufactured by Wako Pure Chemical Industries, Ltd.) were dissolved in a 90 vol % aqueous isopropanol (IPA) solution (42.8 mL) and bubbled with nitrogen gas for 30 minutes. Thereafter, 0.221 g of tris(2-dimethylaminoethyl)amine ($Me_6TREN$) (manufactured by Alfa Aesar) was added to the solution under a nitrogen atmosphere. The reaction solution was stirred for 5 minutes to form a catalyst of $CuCl/CuCl_2/Me_6TREN$. The reaction solution was reacted with the initiator introduced crosslinked polyvinyl alcohol beads under a nitrogen atmosphere at room temperature for 16 hours. After completion of the reaction of ATRP, the beads were washed sequentially with ethanol, a 50 mmol/L-EDTA aqueous solution and pure water in this order to wash away the monomer, polymer and copper catalysts.

3) Introduction of Sulfonate Group

The beads into which a graft chain was introduced by the atom transfer radical polymerization method were placed in 200 g of an aqueous solution mixture of sodium sulfite and IPA (sodium sulfite/IPA/pure water=10/15/75 wt %). A reaction was performed at 80° C. for 24 hours to convert an epoxy group of the graft chain into a sulfonate group. After completion of the reaction, the beads were washed with pure water. Thereafter, the beads were placed in 0.5 mol/L sulfuric acid and a reaction was performed at 80° C. for 2 hours to convert the epoxy group remaining in the graft chain into a diol group. After completion of the reaction, the beads were washed with pure water to obtain the cationic ion exchange carrier of Example 1. A column was packed with the cationic ion exchange carrier.

4) Determination of Copolymerization Proportion

A copolymer was polymerized using a monomer composition containing a precursor monomer of a sulfonate group, glycidyl methacrylate (GMA, manufactured by Tokyo Chemical Industry Co., Ltd.), in a proportion of 1 mol % relative to N-isopropylacrylamide without using a matrix. More specifically, the reaction solution prepared in the above step 2) was reacted with ethyl 2-bromoisobutyrate under a nitrogen atmosphere and ATRP was performed at room temperature for 16 hours. After completion of the reaction, the reaction solution was placed in a dialysis membrane (Spectra/por Dialysis Membrane, MWCO1000, manufactured by Spectrum Laboratories, Inc.) and sequentially soaked in ethanol, a 50 mmol/L-EDTA aqueous solution and pure water in this order to remove monomer and copper catalyst. Subsequently, the reaction solution was lyophilized to obtain a copolymer. The copolymer was placed in 200 g of an aqueous solution mixture of sodium sulfite and IPA (sodium sulfite/IPA/pure water=10/15/75 wt %). A reaction was performed at 80° C. for 24 hours to convert the epoxy group in the graft chain into a sulfonate group. After completion of the reaction, the reaction solution was placed in a dialysis membrane and soaked in pure water to remove sodium sulfite and IPA. The reaction solution was lyophilized to obtain a copolymer.

The above copolymer (30 mg) was dissolved in deuterated water (670 mg) and $^1H$-NMR was measured by use of a nuclear magnetic resonance apparatus (Bruker Avenve-600). Thereafter, from the value of integral of a signal derived from N-isopropylacrylamide unit and the value of integral of a signal derived from a sulfonate group, the copolymerization proportion (composition) of a monomer unit having a strong cation exchange group relative to N-isopropylacrylamide was calculated. As a result, the copolymerization proportion was 0.72 mol %. In addition, it was confirmed by lithium ion exchange that the synthesized resin has a sulfonate group density of 31 mmol/L.

(Preparation of Cell Culture Solution)

A culture supernatant containing AE6F4 antibody (human monoclonal antibody) in an amount of 0.115 mg/L as an antibody protein was prepared. AE6F4 production cells were provided by associate professor, Yoshinori Katakura of Faculty of Agriculture, Kyushu University. AE6F4 antibody production cells were cultured with reference to a document (Summary of Lecture of the Society for Biotechnology, Japan, 1994, Vol. 65, page 65). A culture solution containing AE6F4 antibody production cells was filtered by use of a filtration membrane (trade name: BioOptimal (registered trade mark) MF-SL, manufactured by Asahi Kasei Medical Co., Ltd.) to obtain a solution mixture (culture supernatant) containing impurities and the antibody. The filtration was performed with reference to the instruction manual provided by the provider.

(Purification of Antibody Protein by Protein a Column)

To a protein A column (packed with MabSelect Sure manufactured by GE Healthcare Bio-sciences AB) equilibrated with 150 mL of a phosphate buffer (20 mmol/L sodium phosphate+150 mmol/L NaCl (pH 8.0)), the solution mixture (2 L) filtered was loaded to allow protein A to adsorb the antibody protein. Subsequently, the column was washed with 20 mL of a phosphate buffer (20 mmol/L sodium phosphate+150 mmol/L NaCl (pH 8.0)), and thereafter, 240 mL of an elution buffer (100 mmol/L sodium citrate (pH 3.6)) was supplied to allow the antibody protein to elute from the protein A column. In this way, a solution mixture reduced in amount of impurities to some extent was recovered.

(Virus Inactivation Treatment)

To the obtained elution fraction, 1 mol/L Tris-HCl (pH 8.0) in a volume of 0.5% of the elution fraction was added to control the hydrogen ion exponent (pH) of the elution fraction to be 4. Acetic acid was further added dropwise to the elution fraction to control the hydrogen ion exponent (pH) of the elution fraction to be 3.5. The elution fraction was allowed to stand still for 1 hour to inactivate virus. Thereafter, the hydrogen ion exponent (pH) of the elution fraction was controlled with a tris buffer to be 5.0 and the buffer was exchanged with an acetate buffer (15 mmol/L acetate buffer (pH 6.0)) to obtain solution mixture 1.

The absorbance of solution mixture 1 was measured in the following conditions by size exclusion chromatographic (SEC) apparatus.

Column: Tskgel G3000SWXL (manufactured by Tosoh Corporation)

Column temperature: 30° C.

Pump: LC-20AD (manufactured by Shimadzu Corporation)

Detector: SPD-20A (manufactured by Shimadzu Corporation)

Auto-sampler: SIL-20AC (manufactured by Shimadzu Corporation)

Column oven: CTO-20AC (manufactured by Shimadzu Corporation)

Degasser: DGU-20AC3

Mobile phase: 0.1 mol/L disodium hydrogen-phosphate+ 0.2 mol/L L (+)-arginine aqueous solution (controlled to be pH 6.7 with hydrochloric acid)

Figure 2:
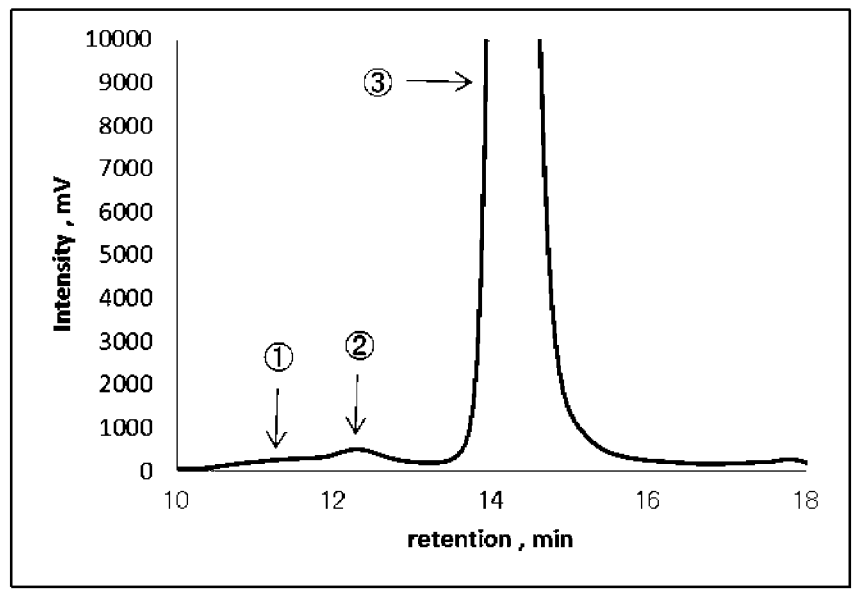
FIG. 2 is a magnified view of the graph of FIG. 1.

As a result, as shown in FIG. 1, the initial rise of an absorption peak was not sharp. This result indicates that not only the monomer of the antibody protein but also aggregate components (impurities) of the antibody protein are included. FIG. 2 shows a magnified view of the peak of FIG. 1. In FIG. 2, the peak of the monomer is indicated by (3) and the peaks of aggregates recovered earlier than the monomer are separately indicated by (1) and (2). The content and content rate of the aggregate component represented by the peak (1) were 0.67 mg and 1.2%, respectively; the content and content rate of the aggregate component represented by the peak (2) were 0.95 mg and 1.7%, respectively; and the content and content rate of the monomer of an antibody protein represented by the peak (3) were 54.44 mg and 97.1%, respectively. The total amount of aggregates and monomer of an antibody recovered was 56.06 mg (solution mixture 1).

(Removal of Aggregate Component)

To the column packed with the cationic ion exchange carrier, the elution fraction (solution mixture 1), which was recovered from the protein A column and subjected to the virus inactivation treatment, was loaded to bring the solution mixture containing the aggregate components (the impurities) and the monomeric component (a desired biologically active substance) of the antibody protein into contact with the cationic ion exchange carrier. The amount of elution fraction added was 12 mL (4.7 mg/mL); the flow rate was 0.4 mL/min; and the temperature was 20° C. Thereafter, the column (packed with the temperature responsive cationic ion exchange carrier) was washed by supplying an acetate buffer (15 mmol/L acetate buffer (pH 6.0)) of 20° C. at a flow rate of 0.4 mL/min. In the flow-through step and the washing step, 32 mL (1.6 mg/mL) of the solution was recovered. The recovered solution was subjected to size exclusion chromatography (SEC). Also in this case, the graph showing absorbance (not shown) showed that not only the monomer of the antibody protein but also the aggregate components (the impurities) of the antibody protein are contained. However, the content of impurities was small, as shown in FIG. 5.

Note that the mass proportions of the aggregate components and the monomeric components contained in the solution mixture (before treated with cationic ion exchange carrier) to those contained in the recovery solution (after treated with cationic ion exchange carrier) were all shown by content rates.

Provided that the total amount of the antibody protein (including the aggregate components and the monomeric component) contained in the protein A elution fraction is regarded as 100%, the percentage of the total amount of the antibody protein (including the aggregate components and the monomeric component) recovered from the column packed with the cationic ion exchange carrier by the flow-through operation was specified as the antibody recovery rate.

The adsorption rate of the aggregates is calculated by dividing the total content of aggregate components (represented by the peaks (1) and (2)) of the flow-through fraction from the column packed with the cationic ion exchange carrier by the total content of aggregate components (represented by the peaks (1) and (2)) of the mixture solution before loading to the column (packed with the cationic ion exchange carrier) to obtain a product; obtaining a value by subtracting the product (calculated above) from 1; and converting the obtained value into percentage. The monomer recovery rate is obtained by dividing the content of the monomer contained in the flow-through fraction from the column (packed with a cationic ion exchange carrier) by the content of the monomer contained in the solution mixture before loading to the column (packed with the cationic ion exchange carrier) to obtain a product and converting the product into percentage.

Example 2

The same operation was repeated as in Example 1 except that the elution fraction (the same composition as in Example 1), which was recovered from the protein A column and subjected to the virus inactivation treatment was brought into contact with the cationic ion exchange carrier stored in the column at 25° C. and washed. The results are shown in FIG. 5.

Example 3

In the aggregate removal step, 46 mL (5.5 mg/mL) of solution mixture 2 (the content rate of the aggregate component represented by the peak (1): 0.5%; the content rate of the aggregate component represented by the peak (2): 1.2%; and the content rate of the monomer of an antibody protein represented by the peak (3): 98.3%) was brought into contact with the cation exchange resin stored in the column at 25° C. and washed. The solution (66 mL (3.6 mg/mL)) was recovered in the flow-through step and the washing step. The same operation was repeated as in Example 2 except for the above conditions. The results are shown in FIG. 5.

Example 4

In Example 4, a cation exchange membrane having a hollow fiber shape and having a sulfonate group was synthesized by a radiation graft polymerization method.

1) Radiation Graft Polymerization

N-isopropylacrylamide (8.090 g), glycidyl methacrylate (0.102 g) and butyl methacrylate (0.208 g) were dissolved in 500 mL of a 25 vol % aqueous t-butyl alcohol (manufactured by Wako Pure Chemical Industries, Ltd.) solution and bubbled with nitrogen gas for 30 minutes to prepare a reaction solution. Polyethylene porous hollow fibers (6.000 g (15 cm, 30 fibers)) having an outer diameter of 3.0 mm, an inner diameter of 2.0 mm and an average pore diameter of 0.25 μm were placed in an airtight container and the air within the container was replaced with nitrogen. Thereafter, the container was irradiated with γ ray (200 kGy) while externally cooling the container with dry ice to generate radicals. The polyethylene porous hollow fibers having radicals were transferred to a glass reaction tube. Oxygen in the reaction tube was removed by reducing pressure to 200 Pa or less. Into this container, the above reaction solution (250 mL) controlled at 40° C. was introduced and allowed to stand still for 16 hours. Thereafter, the hollow fibers were washed with ethanol and dried in a vacuum dryer.

2) Introduction of Sulfonate Group

The hollow fibers, into which a graft chain was introduced by the radiation graft polymerization method, were placed in 200 g of an aqueous solution mixture of sodium sulfite and IPA (sodium sulfite/IPA/pure water=10/15/75 wt %). A reaction was performed at 80° C. for 24 hours to convert an epoxy group in the graft chain into a sulfonate group. After completion of the reaction, the hollow fibers were washed with pure water. Thereafter, the hollow fibers were placed in 0.5 mol/L sulfuric acid and a reaction was performed at 80° C. for 2 hours to convert the epoxy group remaining in the graft chain into a diol group. This was modularized (membrane volume: 0.6 mL) to obtain the cation exchange membrane of Example 3.

3) Detection of N-Isopropylacrylamide

N-isopropylacrylamide was detected by pyrolytic GC/MS in the following conditions.

Thermolysis apparatus: PY2020D (manufactured by Frontier Laboratories Ltd.)

Thermolysis temperature: 600° C.

GC apparatus: Agilent 6890 (manufactured by Agilent Technologies, Inc.)

MS apparatus: Agilent 6973 (manufactured by Agilent Technologies, Inc.)

Column: DB-1 (manufactured by Agilent Technologies, Inc.)

0.25 mm i.d.×30 m Liquid-phase thickness: 0.25 μm

Column temperature: 40° C. (maintained for 5 minutes) →(a temperature increase rate: 20° C./minute)→320° C. (maintained for 11 min)

Inlet temperature: 320° C.

Split ratio: 1/100

Column flow rate: 1.0 mL/minute (helium)

Ionization method: electron ionization (EI method)

Detection time of isopropyl amine site: 1 minute and 24 seconds

Detection time of isopropyl isocyanate: 1 minute and 46 seconds

Detection time of N-isopropylacrylamide monomer site: 8 minutes and 9 seconds

An antibody protein was purified by the protein A column and virus was inactivated in the same manner as in Example 1. The buffer of an elution fraction was exchanged with a 15 mol/L acetate buffer (pH 6.0) to obtain solution mixture 3.

The absorbance of solution mixture 3 was measured by a size exclusion chromatographic (SEC) apparatus in the following conditions.

Column; ACQUITY YPLC BEH200 SEC 1.7 μm (manufactured by Waters Corporation)

Column temperature: 30° C.

System: ACQUITY UPLC H CLASS (manufactured by Waters Corporation)

Mobile phase: 0.1 mol/L disodium hydrogen-phosphate+ 0.2 mol/L L (+)-aqueous arginine solution (controlled to be pH 6.7 with hydrochloric acid)

Figure 3:
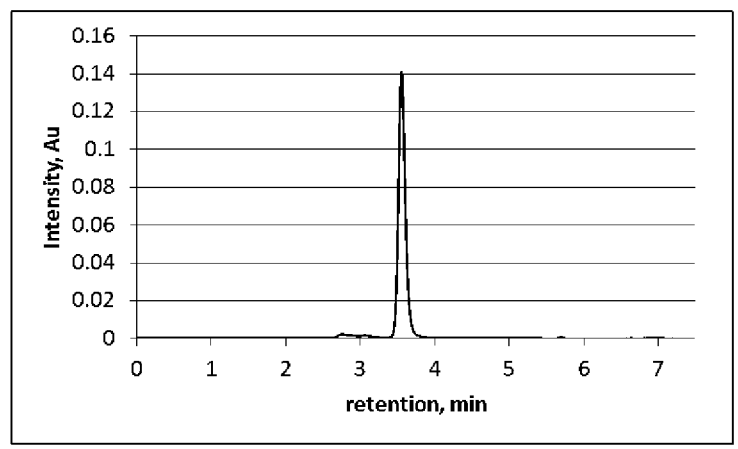
FIG. 3 is a graph showing absorbance obtained by subjecting an elution fraction from a protein A column according to Example 3 to size exclusion chromatography.
Figure 4:
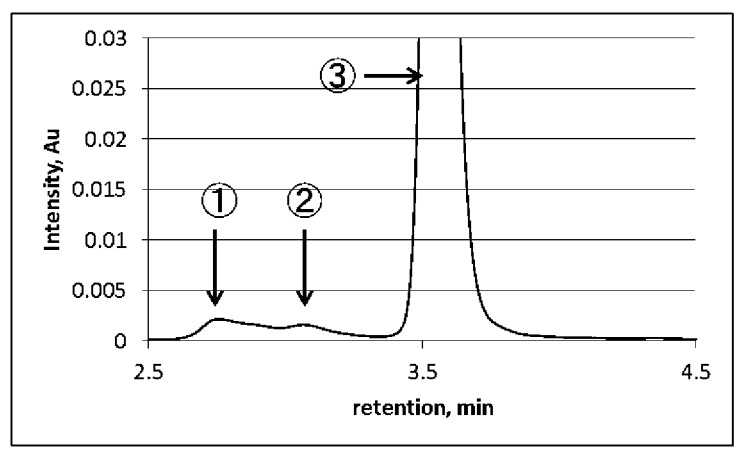
FIG. 4 is a magnified view of the graph of FIG. 3.

As a result, the peak was obtained as shown in FIG. 3 and magnified in FIG. 4. Note that, in Example 3, absorbance was measured by a different apparatus from that used in Examples 1 and 2. The equivalence of the apparatuses was confirmed. As shown in FIG. 4, the peak of the monomer is indicated by (3) and the peaks of aggregates recovered earlier than the monomer are separately indicated by (1) and (2). The content and content rate of the aggregate component represented by the peak (1) were 1.41 mg and 1.9%, respectively; the content and content rate of the aggregate component represented by the peak (2) were 1.11 mg and 1.5%, respectively; and the content and content rate of the monomer of an antibody protein represented by the peak (3) were 71.65 mg and 96.6%, respectively. The total amount of aggregates and monomer of the antibody recovered was 74.17 mg.

(Removal of Aggregate Component)

To the cation exchange membrane modularized, the elution fraction (solution mixture 3), which was recovered from the protein A column and subjected to the virus inactivation treatment was loaded to bring the solution mixture containing the aggregate components (the impurities) and the monomeric component (a desired biologically active substance) of the antibody protein into contact with the cation exchange membrane. The amount of elution fraction added was 15 mL (4.9 mg/mL); the flow rate was 6.0 mL/min; and the temperature was 35° C. Thereafter, the cation exchange membrane modularized was washed by supplying an acetate buffer (15 mmol/L acetate buffer (pH 6.0)) of 35° C. at a flow rate of 6.0 mL/min. In the flow-through step and the washing step, 27 mL (2.3 mg/mL) of the solution was recovered. The recovered solution was subjected to size exclusion chromatography (SEC). Also in this case, the graph showing absorbance (not shown) showed that not only the monomer of the antibody protein but also the aggregate components (the impurities) of the antibody protein were contained. However, the content of impurities was small, as shown in FIG. 5.

Example 5

In Example 5, the same operation was repeated as in Example 4 except that the aggregate removal step was carried out using solution mixture 4 (the content rate of the aggregate component represented by the peak (1): 1.5%; the content rate of the aggregate component represented by the peak (2): 0.9%; and the content rate of the monomer of an antibody protein represented by the peak (3): 97.6%) at 30° C. The results are shown in FIG. 5. Note that aggregate removal performance deteriorates compared to the results at a temperature of 35° C. in Example 4. As is apparent from this, if the temperature is lowered when hollow fiber-like cation exchange membrane of Example 4 is used, aggregate removal performance deteriorates. Therefore, the hollow fiber-like cation exchange membrane is not suitably used at room temperature.

Example 6

In Example 6, the same operation was repeated as in Example 5 except that a solution dissolving N-isopropylacrylamide (5.380 g), glycidyl methacrylate (0.098 g) and butyl methacrylate (2.939 g) in 500 mL of a 50 vol % aqueous t-butyl alcohol (manufactured by Wako Pure Chemical Industries, Ltd.) solution was used in the radiation graft polymerization, and that solution mixture 5 (the content rate of the aggregate component represented by the peak (1): 2.1%; the content rate of the aggregate component represented by the peak (2): 1.1%; and the content rate of the monomer of an antibody protein represented by the peak (3): 96.8%) was used in the aggregate removal step. The results are shown in FIG. 5.

Example 7

In Example 7, the same operation was repeated as in Example 6 except that a solution dissolving N-isopropylacrylamide (5.187 g), glycidyl methacrylate (0.292 g) and butyl methacrylate (2.919 g) in 500 mL of a 50 vol % aqueous t-butyl alcohol (manufactured by Wako Pure Chemical Industries, Ltd.) solution was used in the radiation graft polymerization, and that solution mixture 6 (the content rate of the aggregate component represented by the peak (1): 2.0%; the content rate of the aggregate component represented by the peak (2): 1.7%; and the content rate of the monomer of an antibody protein represented by the peak (3): 96.3%) was used in the aggregate removal step. The results are shown in FIG. 5.

Example 8

In Example 8, 140 mL of a solution dissolving N-isopropylacrylamide (3.6 g), glycidyl methacrylate (0.6 g) and butyl methacrylate (1.8 g) in 280 mL of a 50 vol % aqueous t-butyl alcohol (manufactured by Wako Pure Chemical Industries, Ltd.) solution was used in the radiation graft polymerization and reacted with polyethylene porous fibers (3.000 g (15 cm, 15 fibers)). Thereafter, a cation exchange membrane was synthesized by sulfonation and modularized so as to have a membrane volume of 0.25 mL. In the aggregate removal step, 20 mL (5.1 mg/mL) of solution mixture 7 (the content rate of the aggregate component represented by the peak (1): 4.0%; the content rate of the aggregate component represented by the peak (2): 2.8%; and the content rate of the monomer of an antibody protein represented by the peak (3): 93.2%) was added. The flow rate was 1.5 mL/min and the temperature was 25° C. Thereafter, the cation exchange membrane modularized was washed by supplying an acetate buffer (15 mmol/L acetate buffer (pH 6.0)) of 25° C. at a flow rate of 1.5 mL/min. The solution (27.5 mL (3.1 mg/mL) was recovered in the flow-through step and the washing step. The same operation was repeated as in Example 6 except the above conditions. The results are shown in FIG. 5.

Example 9

In Example 9, 20 mL (5.0 mg/mL) of solution mixture 8 obtained by exchanging the buffer with 15 mmol/L tris buffer (pH 7.0) (the content rate of the aggregate component represented by the peak (1): 2.3%; the content rate of the aggregate component represented by the peak (2): 2.4%; and the content rate of the monomer of an antibody protein represented by the peak (3): 95.4%) was added in the aggregate removal step. The flow rate was 1.5 mL/min and the temperature was 25° C. Thereafter, the cation exchange membrane modularized was washed by supplying a tris buffer (15 mmol/L tris buffer (pH 7.0)) of 25° C. at a flow rate of 1.5 mL/min. The solution (27.5 mL (2.9 mg/mL)) was recovered in the flow-through step and the washing step. The same operation was repeated as in Example 8 except for the above conditions. The results are shown in FIG. 5.

Example 10

In Example 10, 20 mL (4.8 mg/mL) of solution mixture 9 obtained by exchanging the buffer with 15 mmol/L tris buffer (pH 8.0) (the content rate of the aggregate component represented by the peak (1): 1.6%; the content rate of the aggregate component represented by the peak (2): 2.3%; and the content rate of the monomer of an antibody protein represented by the peak (3): 96.1%) was added in the aggregate removal step. The flow rate was 1.5 mL/min and the temperature was 25° C. Thereafter, the cation exchange membrane modularized was washed by supplying a tris buffer (15 mmol/L tris buffer (pH 8.0)) of 25° C. at a flow rate of 1.5 mL/min. The solution (27.5 mL (2.9 mg/mL)) was recovered in the flow-through step and the washing step. The same operation was repeated as in Example 8 except for the above conditions. The results are shown in FIG. 5.

Example 11

In Example 11, 140 mL of a solution dissolving N-isopropylacrylamide (3.6 g), glycidyl methacrylate (1.2 g) and butyl methacrylate (1.2 g) in 280 mL of a 50 vol % aqueous t-butyl alcohol (manufactured by Wako Pure Chemical Industries, Ltd.) solution was used in the radiation graft polymerization and reacted with polyethylene porous fibers (3.000 g (15 cm, 15 fibers)). Thereafter, a cation exchange membrane was synthesized by sulfonation and modularized so as to have a membrane volume of 0.25 mL. It was confirmed by lithium ion exchange that the synthesized membrane has a sulfonate group density of 35 mmol/L. In the aggregate removal step, 25 mL (5.2 mg/mL) of solution mixture 10 (the content rate of the aggregate component represented by the peak (1): 1.8%; the content rate of the aggregate component represented by the peak (2): 2.8%; and the content rate of the monomer of an antibody protein represented by the peak (3): 95.4%) was added. The flow rate was 0.3 mL/min and the temperature was 25° C. Thereafter, the cation exchange membrane modularized was washed by supplying an acetate buffer (15 mmol/L acetate buffer (pH 6.0)) of 25° C. at a flow rate of 0.3 mL/min. The solution (32.5 mL (3.2 mg/mL)) was recovered in the flow-through step and the washing step. The same operation was repeated as in Example 8 except for the above conditions. The results are shown in FIG. 5.

Example 12

In Example 11, 140 mL of a solution dissolving N-isopropylacrylamide (3.6 g), glycidyl methacrylate (1.3 g) and butyl methacrylate (1.1 g) in 280 mL of a 50 vol % aqueous t-butyl alcohol (manufactured by Wako Pure Chemical Industries, Ltd.) solution was used in the radiation graft polymerization and reacted with polyethylene porous fibers (3.000 g (15 cm, 15 fibers)). Thereafter, a cation exchange membrane was synthesized by sulfonation and modularized so as to have a membrane volume of 0.25 mL. It was confirmed by lithium ion exchange that the synthesized membrane has a sulfonate group density of 41 mmol/L. In the aggregate removal step, 25 mL (5.0 mg/mL) of solution mixture 11 (the content rate of the aggregate component represented by the peak (1): 1.5%; the content rate of the aggregate component represented by the peak (2): 2.3%; and the content rate of the monomer of an antibody protein represented by the peak (3): 96.2%) was added. The flow rate was 0.3 mL/min and the temperature was 25° C. Thereafter, the cation exchange membrane modularized was washed by supplying an acetate buffer (15 mmol/L acetate buffer (pH 6.0)) of 25° C. at a flow rate of 0.3 mL/min. The solution (32.5 mL (3.1 mg/mL) was recovered in the flow-through step and the washing step. The same operation was repeated as in Example 8 except for the above conditions. The results are shown in FIG. 5.

As shown in FIG. 5, in Examples 1 to 12, the content of the aggregate component represented by the peak (1) and the content of the aggregate component represented by the peak (2) can be reduced to less than 50% by the ion exchange chromatography carrier. From this, it was demonstrated that impurities can be adsorbed to the carrier in a mass proportion of 50% or more at 20° C., 25° C., 30° C. and 35° C. It was also demonstrated that 70% or more of the monomer of the antibody can be recovered. It was further demonstrated that the mass proportion (content rate) of impurities (total of aggregate component 1 and aggregate component 2) relative to the mass of the solution recovered is 2% or less.

According to the method of the embodiment, a monomer of an antibody protein can be purified by changing temperature on an industrial scale.

What is claimed is:

1. A method for purifying a biologically active substance from a solution mixture containing impurities and the biologically active substance, wherein
   an ion exchange chromatography carrier having a matrix and a copolymer containing at least N-isopropylacrylamide as a monomer unit and immobilized to a surface of the matrix is used,
   the mass portion of N-isopropylacrylamide in the copolymer is 0.30% to 70%, and
   the solution mixture is allowed to flow through a container storing the carrier at a uniform temperature to selectively adsorb the impurities, thereby recovering the biologically active substance.

2. The method according to claim 1, wherein the uniform temperature is a temperature at which the impurities can be adsorbed in a mass fraction of 50% or more to the carrier and the biologically active substance can be recovered in a mass fraction of 70% or more.

3. The method according to claim 1, wherein the mass proportion of the impurities relative to the mass of a solution recovered from the container storing the carrier is 2% or less.

4. The method according to claim 1, wherein the temperature is 5° C. or more and 60° C. or less.

5. The method according to claim 1, wherein the temperature is 20° C. or more and 35° C. or less.

6. The method according to claim 1, wherein the solution mixture is allowed to flow through at a flow rate of 0.1 times or more the volume of the ion exchange chromatography carrier/minute and 30 times or less the volume of the carrier/minute.

7. The method according to claim 1, wherein the solution mixture is allowed to flow through at a flow rate of the same as or more than the volume of the ion exchange chromatography carrier/minute and 10 times or less the volume of the carrier/minute.

8. The method according to claim 1, wherein the biologically active substance is a monomer of an antibody protein.

9. The method according to claim 8, wherein the impurities are aggregate components of a dimer or a multimer of the antibody protein.

10. The method according to claim 1, wherein the ion exchange chromatography carrier is a cation exchange carrier in the form of beads.

11. The method according to claim 1, wherein the ion exchange chromatography carrier is a cation exchange carrier in the form of membrane.

12. The method according to claim 11, wherein the cation exchange carrier is a hollow fiber membrane.

13. The method according to claim 1, further comprising, before the solution mixture is allowed to flow through the container storing the ion exchange chromatography carrier,
   purifying the solution mixture by affinity chromatography.

14. The method according to claim 13, wherein a protein A carrier is used in the affinity chromatography.

15. The method according to claim 13, wherein an acid elution type affinity chromatography carrier is used in the affinity chromatography.

16. The method according to claim 13, wherein a temperature responsive affinity chromatography carrier is used in the affinity chromatography.

17. The method according to claim 1, wherein, in the purification method, a buffer used as a mobile phase has a conductivity of 0.5 to 20 mS/cm.

18. The method according to claim 1, wherein, in the purification method, a buffer used as a mobile phase has a hydrogen ion exponent within the range of pH 3.0 to pH 9.0.

19. The method according to claim 1, wherein
   the ion exchange chromatography carrier has a copolymer having at least a strong cation exchange group, and
   the copolymer contains the strong cation exchange group in a proportion of 0.01 mol % to 500.0 mol % relative to N-isopropylacrylamide in terms of monomer.

20. The method according to claim 1, wherein
   the ion exchange chromatography carrier has a copolymer having at least a strong cation exchange group, and
   the copolymer contains the strong cation exchange group in a proportion of 1 mol % to 300.0 mol % relative to N-isopropylacrylamide in terms of monomer.

21. The method according to claim 19, wherein at least part of the monomer unit of the copolymer having the strong cation exchange group is an acrylic acid derivative or a methacrylic acid derivative and has a group represented by the following formula (1) or (2):

$$-CH(-OH)-CH_2-SO_3H \quad (1)$$

$$-CH(-SO_3H)-CH_2-OH \quad (2).$$

22. The method according to claim 19, wherein at least part of the monomer unit of the copolymer having the strong cation exchange group is derived from a vinyl monomer having a sulfonate group.

23. The method according to claim 19, wherein at least part of the monomer unit of the copolymer having the strong cation exchange group is represented by the following formula (3):

$$-CR_1R_2-CR_3(-SO_3H)- \quad (3)$$

where $R_1$, $R_2$ and $R_3$ each individually represent H or Me.

24. The method according to claim 1, wherein
   the ion exchange chromatography carrier has a copolymer having at least a strong cation exchange group, and
   the copolymer is formed by polymerizing a monomer composition containing a monomer having the strong cation exchange group and/or a strong cation exchange group introducing precursor monomer in a proportion of 0.01 mol % to 500.0 mol % relative to N-isopropylacrylamide, by a polymerization method.

25. The method according to claim 1, wherein
the ion exchange chromatography carrier has a copolymer having at least a strong cation exchange group, and
the copolymer is formed by polymerizing a monomer composition containing a monomer having the strong cation exchange group and/or a strong cation exchange group introducing precursor monomer in a proportion of 1 mol % to 300.0 mol % relative to N-isopropylacrylamide, by a polymerization method.

26. The method according to claim 24, wherein at least part of the monomer unit of the copolymer having the strong cation exchange group is an acrylic acid derivative or a methacrylic acid derivative and has a group represented by the following formula (4) or (5):

$$—CH(—OH)—CH_2—SO_3H \quad (4)$$

$$—CH(—SO_3H)—CH_2—OH \quad (5).$$

27. The method according to claim 24, wherein at least part of the strong cation exchange group introducing precursor monomer is an acrylic acid derivative or a methacrylic acid derivative and the copolymer has a side chain represented by the following formula (6) or (7):

$$—CH(—OH)—CH_2—SO_3H \quad (6)$$

$$—CH(—SO_3H)—CH_2—OH \quad (7).$$

28. The method according to claim 24, wherein at least part of a monomer unit of the copolymer having the strong cation exchange group is derived from a vinyl monomer having a sulfonate group.

29. The method according to claim 24, wherein at least part of the monomer having the strong cation exchange group is a vinyl monomer having a sulfonate group.

30. The method according to claim 24, wherein at least part of the monomer unit of the copolymer having the strong cation exchange group is represented by the following formula (8):

$$—CR_1R_2—CR_3(—SO_3H)— \quad (8)$$

where $R_1$, $R_2$ and $R_3$ each individually represent H or Me.

31. The method according to claim 19, wherein the strong cation exchange group is a sulfonate group.

32. The method according to claim 19, wherein the density of the cation exchange group is 30 mmol/L or more.

33. The method according to claim 24, wherein the polymerization method is a surface living radical polymerization method.

34. The method according to claim 24, wherein the polymerization method is a radiation graft polymerization method.

35. A method for purifying a biologically active substance from a solution mixture containing impurities and the biologically active substance, wherein
an ion exchange chromatography carrier having a matrix and a copolymer containing at least N-isopropylacrylamide as a monomer unit and immobilized to a surface of the matrix is used,
the mass portion of N-isopropylacrylamide in the copolymer is 30% to 70%, and
the solution mixture is allowed to flow through a container storing the carrier at a uniform temperature to selectively adsorb the impurities, thereby removing the impurities.

36. An ion exchange chromatography carrier, which is a cation exchange carrier, comprising a matrix and a copolymer containing at least N-isopropylacrylamide as a monomer unit and immobilized to a surface of the matrix, wherein
the mass portion of N-isopropylacrylamide in the copolymer is 30% to 70%,
the copolymer has at least a strong cation exchange group, and
the copolymer is formed by polymerizing a monomer composition containing a monomer having the strong cation exchange group and/or a strong cation exchange group introducing precursor monomer in a proportion of 0.01 to 500.00 mol % relative to N-isopropylacrylamide, by a polymerization method.

37. An ion exchange chromatography carrier, which is a cation exchange carrier, comprising a matrix and a copolymer containing at least N-isopropylacrylamide as a monomer unit and immobilized to a surface of the matrix, wherein
the mass portion of N-isopropylacrylamide in the copolymer is 30% to 70%, and
the copolymer has at least a strong cation exchange group.

* * * * *